(12) United States Patent
Kobayashi et al.

(10) Patent No.: US 11,090,234 B2
(45) Date of Patent: Aug. 17, 2021

(54) FOAM, SCREEN FOAMER COMPOSITION, AND EVALUATION METHOD FOR SAME

(71) Applicant: POLA PHARMA INC., Tokyo (JP)

(72) Inventors: Hirokazu Kobayashi, Kanagawa (JP); Takaaki Masuda, Kanagawa (JP); Nobuo Kubota, Kanagawa (JP); Kahori Fujii, Kanagawa (JP)

(73) Assignee: POLA PHARMA INC., Tokyo (JP)

( * ) Notice: Subject to any disclaimer, the term of this patent is extended or adjusted under 35 U.S.C. 154(b) by 17 days.

(21) Appl. No.: 16/309,722

(22) PCT Filed: Jun. 9, 2017

(86) PCT No.: PCT/JP2017/021515
§ 371 (c)(1),
(2) Date: Dec. 13, 2018

(87) PCT Pub. No.: WO2017/217337
PCT Pub. Date: Dec. 21, 2017

(65) Prior Publication Data
US 2019/0133894 A1    May 9, 2019

(30) Foreign Application Priority Data
Jun. 16, 2016  (JP) .............................. JP2016-120286

(51) Int. Cl.
*A61K 8/04* (2006.01)
*A61K 47/10* (2017.01)
(Continued)

(52) U.S. Cl.
CPC ................ *A61K 8/046* (2013.01); *A61K 8/02* (2013.01); *A61K 8/11* (2013.01); *A61K 8/345* (2013.01);
(Continued)

(58) Field of Classification Search
CPC . A61K 8/02; A61K 8/046; A61K 9/12; G01N 21/59
See application file for complete search history.

(56) References Cited

U.S. PATENT DOCUMENTS

| 10,265,268 B2* | 4/2019 | Kobayashi ............. A61K 47/22 |
| 2019/0133894 A1* | 5/2019 | Kobayashi ............. G01N 21/17 |

FOREIGN PATENT DOCUMENTS

| GN | 105392473 A | 3/2016 |
| GN | 105392473 B | 6/2018 |

(Continued)

OTHER PUBLICATIONS

English language machine translation of JP 2015-203029 to Masuda et al. Obtained from https://www.j-platpat.inpit.go.jp/ on Jul. 17, 2020.*

(Continued)

*Primary Examiner* — Michael A Salvitti
(74) *Attorney, Agent, or Firm* — Hamre, Schumann, Mueller & Larson, P.C.

(57) ABSTRACT

Provided is a product exhibiting good bubbles even from a screen foamer composition using a non-ionic surfactant. This foam contains a non-ionic surfactant and is composed of an air layer and a bubble shell encapsulating the air layer. The bubble shell has a high light transmission region which is optically transparent and a low light transmission region which is less optically transparent than the highlight transmission region, both regions being disposed so as to spread across a surface of the bubble shell in such a manner as to form an identifiable boundary therebetween; and when the foam is allowed to stand at 25° C., an area of the low light transmission region occupying the surface area of the bubble (Continued)

shell expands over time, and thus the entire surface of the bubble shell becomes occupied by the low light transmission region.

16 Claims, 4 Drawing Sheets

(51) Int. Cl.
    *A61K 47/36*     (2006.01)
    *G01N 21/17*     (2006.01)
    *A61K 8/02*     (2006.01)
    *A61K 8/86*     (2006.01)
    *A61K 47/14*     (2017.01)
    *A61K 9/12*     (2006.01)
    *A61K 8/11*     (2006.01)
    *A61K 8/34*     (2006.01)
    *A61K 8/73*     (2006.01)
    *G01N 21/59*     (2006.01)

(52) U.S. Cl.
    CPC ................ *A61K 8/73* (2013.01); *A61K 8/86* (2013.01); *A61K 9/12* (2013.01); *A61K 9/122* (2013.01); *A61K 47/10* (2013.01); *A61K 47/14* (2013.01); *A61K 47/36* (2013.01); *G01N 21/17* (2013.01); *G01N 21/59* (2013.01)

(56) References Cited

FOREIGN PATENT DOCUMENTS

| | | |
|---|---|---|
| JP | 10-158122 | 6/1998 |
| JP | 2004-277365 | 10/2004 |
| JP | 2005068084 A * | 3/2005 |
| JP | 2005-213230 | 3/2006 |
| JP | 2006-069912 | 3/2006 |
| JP | 2006-083093 | 3/2006 |
| JP | 2007-314494 | 12/2007 |
| JP | 2012-214422 | 11/2012 |
| JP | 2013-170145 | 9/2013 |
| JP | 2014-101333 | 6/2014 |
| JP | 2014-125436 | 7/2014 |
| JP | 2014-218470 | 11/2014 |
| JP | 2015-157803 | 9/2015 |
| JP | 2015-157804 | 9/2015 |
| JP | 2015-157805 | 9/2015 |
| JP | 2015-168654 | 9/2015 |
| JP | 2015-203029 | 11/2015 |
| JP | 2015-221783 | 12/2015 |
| WO | 2015/005419 | 1/2015 |
| WO | 2016/104661 | 6/2016 |

OTHER PUBLICATIONS

Kwetkat et al, "Formulation of Homogeneous O/W Emulsion Pump Foams", Speciality Chemicals, Redhill, GB, vol. 25, No. 9, Jan. 1, 2005, pp. 38-39.
Extended European Search Report issue in corresponding European Application No. 17813234.6, dated Dec. 13, 2019, 8 pages.

* cited by examiner (a)    (b)

|  | Composition 1 | Composition 2 | Composition 3 |
|---|---|---|---|
| Microscope (immediately after preparation) | | | |
| Microscope (Stand for 1 hour) | | | |
| Microscope (Centrifuged) | | | |
| Microscope (Foam) | | | |
| Form of foam (Naked eye) | | | |

Micelle component in phase inversion, absorbed on the two-phase three-layer membrane Two-phase three-layer structure

FOAM, SCREEN FOAMER COMPOSITION, AND EVALUATION METHOD FOR SAME

TECHNICAL FIELD

The present invention relates to foam, a screen foamer composition for forming the foam, and an evaluation method for the composition.

BACKGROUND ART

A foaming external composition has been used for a long time since there are great advantages of foam such as softness when administered on the skin, the occlusive effect and high specific surface area of foam (for example, see Patent Literature 1). A prototype of the foaming external composition is a formulation that sprays a composition having a low surface tension together with a liquefied gas which forms foam due to vaporization and volumetric expansion of liquefied gas. Previously, fluorine compounds such as Freon and the like were used as liquefied gases. In recent years, a fluorine gas is not available because of the concern of expanding an ozone hole and thus, the fluorine gas is replaced by a liquefied natural gas. However, the liquefied natural gas has problems such as the liquefied natural gas itself irritates to the skin (see, for example, Patent Literature 2), and handling is troublesome as it is a combustible explosive substance. Thus, it is substantially difficult for the liquefied natural gas to be practically applied to products.

In such situation, a foaming technology instead of utilizing a gas but by applying pressure to pass a composition through a screen has been developed and applied to cleaning products and the like (see, for example, Patent Literature 3 and Patent Literature 4). In the cleaning products and the like, ionic surfactants such as anionic surfactants and the like are used as active ingredients for cleaning and foaming. This is because the ionic surfactant forms a double-layer having a strong structure in which hydrophobic groups of the surfactant each other orients toward the inside (see FIG. 1), thereby stabilizing bubbles to improve the generation of bubbles. Therefore, when observing the bubbles with a microscope, only the double-layer structure of a bubble shell is visible, and a plurality of structures dividing the bubble shell in the spreading direction of the surface are not observed. It is because one double-layer is closed, and the closed space contains air to form a bubble. This is due to two factors of which a small sized hydrophilic group with high hydrophilicity and a large sized hydrophobic group in the ionic surfactants. As compared to the ionic surfactants, non-ionic surfactants have a large sized hydrophilic group with low hydrophilicity and partially have a hydrophobic moiety, which cannot have a double-layer structure like the ionic surfactants, and the bubble shell strength is not sufficient. Thus, it has been considered that satisfactory foamability cannot be obtained by a foam generating means such as a screen foamer. Therefore, the screen foamer composition was only applied to cleaning products.

In such situation, a composition having excellent foamability even with the screen foamer has been found (see, for example, Patent Literature 5 and Patent Literature 6). However, the reason is not clear, and any specific non-ionic surfactant capable of obtaining excellent foamability is not clearly stated. Therefore, application to an external preparation for skin which does not require a washing step has been limited.

In addition, it is common to generate foam by using an ionic surfactant to pass a composition not containing hydrophobic ingredients through a screen foamer. However, a screen foamer composition, in which a non-ionic surfactant is contained as a foam-forming agent and all ingredients other than the surfactant are hydrophilic, is not known at all.

Therefore, although attempts have been desired to contain a moisturizing component in a screen foamer composition consisting solely of a hydrophilic ingredient and forming foam through a screen foamer to administer the composition without any physical irritation to the skin, which is likely to be irritated, such as rough skin or the like, but have not done at all.

CITATION LIST

Patent Literature

Patent Literature 1: JP 2007-314494 A
Patent Literature 2: JP H10-158122 A
Patent Literature 3: JP 2014-218470 A
Patent Literature 4: JP 2005-213230 A
Patent Literature 5: JP 2006-083093 A
Patent Literature 6: JP 2004-277365 A

SUMMARY OF INVENTION

Technical Problem

In such situation, an object of the present invention is to provide novel foam capable of administering water-soluble active ingredients with less physical irritation on skin which is easily irritated, such as rough skin or the like, and a screen foamer composition used for forming the foam. Further, another object of the present invention is to provide an evaluation method for a screen foamer composition forming the foam.

Solution to Problem

In view of the situation, the present inventors intensively researched a foam structure using a highly safe non-ionic surfactant as a foam forming agent, and as a result, found that good stability is obtained in foam in which a surface of the foam has a high light transmission region and a low light transmission region, and an area of the low light transmission region expands over time under stationary condition so that an entire foam surface has a property of being occupied by the low light transmission region.

In other words, the present invention for solving the above problems is described as follows.

To solve the above problem, according to the present invention, there is provided foam containing a non-ionic surfactant and composed of an air layer and a bubble shell encapsulating the air layer, wherein the bubble shell has a transmission region which is optically transparent and a low light transmission region which is less optically transparent than the high light transmission region, both regions being disposed so as to spread across a surface of the bubble shell in such a manner as to form an identifiable boundary therebetween, and when the foam is allowed to stand at 25° C., an area of the low light transmission region occupying the surface area of the bubble shell expands over time, and thus the entire surface of the bubble shell becomes occupied by the low light transmission region.

The foam of the present invention has high safety and is excellent in foam stability.

In a preferred embodiment of the present invention, a structure of the bubble shell in the low light transmission region is a multilayer structure composed of two or more layers.

In a more preferred embodiment of the present invention, the multilayer structure is a two-phase three-layer structure containing:

an aqueous component phase in contact with an outer gas phase of the foam;

an aqueous component phase in contact with an inner gas phase of the foam; and a droplet phase interposed between the two aqueous component phases and containing a non-ionic surfactant and a polyhydric alcohol having a hydrophobic end and/or a polyhydric alcohol polymer.

A foam in which a structure of the bubble shell in such a low light transmission region is a multilayer structure is excellent in foam stability.

Furthermore, to solve the above problem, according to the present invention, there is provided a screen foamer composition comprising a non-ionic surfactant as a foam forming agent and being in a solubilized state capable of forming the foam according to any one of claims 1 to 3 by a screen foamer.

The composition of the present invention is preferable for forming the foam of the present invention described above.

In a preferred embodiment of the present invention, the composition contains a polysaccharide which may be sulfated at an amount of 0.001 to 5% by mass.

A composition in which a content of polysaccharide which may be sulfated is within the above range can stabilize a structure of the formed foam in the low light transmission region.

In a preferred embodiment of the present invention, the polysaccharide which may be sulfated is a heparin-like substance and/or hyaluronic acid.

In a preferred embodiment of the present invention, the composition contains 1 to 15% by mass of a non-ionic surfactant.

The composition in which the concentration of the non-ionic surfactant is within the above range is more preferable for forming the foam of the present invention.

In a preferred embodiment of the present invention, the composition contains 10% by mass or more of a polyhydric alcohol having a hydrophobic end and/or a polyhydric alcohol polymer.

By setting the concentration of the polyhydric alcohol having a hydrophobic end and/or polyhydric alcohol polymer within the above range, the structure of the formed foam in the low light transmission region can be stabilized. In addition, the feeling of use such as moisturizing feeling or the like can be improved.

In a preferred embodiment of the present invention, the composition contains 0.001 to 30% by mass of the polyhydric alcohol having 2 to 6 carbon atoms in which hydroxyl groups are bonded to all the carbon atoms.

By setting the concentration of the polyhydric alcohol within the above range, the structure of the formed foam in the low light transmission region can be stabilized. In addition, the feeling of use such as moisturizing feeling, or the like, can be improved.

Further, in a preferred embodiment of the present invention, the composition contains an organic salt and/or an inorganic salt.

The composition of the present invention in the form of containing an organic salt and/or an inorganic salt is more preferable for forming the foam of the present invention.

In a preferred embodiment of the present invention, the composition is prepared by solubilizing ingredients thereof at or above the cloud point of the non-ionic surfactant.

The composition obtained by solubilizing at or above the cloud point is more preferable for forming the foam of the present invention.

In a preferred embodiment of the present invention, the composition satisfies the following conditions (A) and (B) when observed by an optical microscope:

(A) before the treatment of (I) or (II) below, no micelle image is observed or a micelle image is hardly observed, and (B) after the treatment of (I) below, the micelle image is observed:

(I) the composition is allowed to stand in an open system, and (II) stress is applied to the composition.

The composition that satisfies the conditions (A) and (B) above is preferable for forming the foam of the present invention.

In a preferred embodiment of the present invention, the composition further satisfies the following condition (C):

(C) after the treatment of (II) above, the micelle images are more observed than before the treatment.

The composition satisfying the above condition (C) is more preferable for forming the foam of the invention.

In a preferred embodiment of the present invention, the composition satisfies the above conditions when stress is applied to the composition by centrifugation as the treatment (II).

The composition that satisfies the above conditions when stress is applied by centrifugation is more preferable for forming the foam of the present invention.

Further, the present invention relates to a preparation method for a screen foamer composition of the present invention, in which ingredients of the composition are solubilized at or above the cloud point of the non-ionic surfactant.

By the preparation method, it is possible to prepare a more suitable composition as a screen foamer composition which forms the foam of the present invention.

Further, the present invention relates to an evaluation method for a screen foamer composition using a non-ionic surfactant as a foam forming agent. In the method, when the composition is passed through a screen foamer to form a foam, in the bubble shell, a high light transmission region which is optically transparent and a low light transmission region which is less optically transparent than the high light transmission region are observed, both regions being disposed so as to spread across a surface of the bubble shell in such a manner as to form an identifiable boundary therebetween. In a case where it is confirmed that when the foam is allowed to stand at 25° C., an area of the low light transmission region occupying the surface area of the bubble shell expands over time so that the entire surface of the bubble shell becomes occupied by the low light transmission region, the foam is determined as being suitable as a screen foamer composition, and in a case where it is not confirmed that when the foam is allowed to stand at 25° C., an area of the low light transmission region occupying the surface area of the bubble shell expands over time so that the entire surface of the bubble shell becomes occupied by the low light transmission region, the foam is determined as being unsuitable as a screen foamer composition.

When using the evaluation method of the present invention, it is possible to determine whether or not the composition is suitable as a screen foamer composition. Thus, it is possible to provide a foam forming preparation which is excellent in foamability and foam stability by selecting a suitable composition.

In a preferred embodiment of the present invention, the observation of the high light transmission region and the low light transmission region is performed by an optical microscope.

By observing using an optical microscope, it is possible to easily or precisely determine whether or not it is suitable as a screen foamer composition.

The composition is determined as being more suitable as a screen foamer composition as a difference between the maximum diameter and the minimum diameter of the high light transmission region is smaller, which is observed in a process of expanding an area of the low light transmission region occupying the surface area of the bubble shell over time when the foam is allowed to stand at 25° C.

By using these criteria, more accurate evaluation can be conducted.

In a preferred embodiment of the present invention, when the composition is observed by an optical microscope without passing through the screen foamer, and in a case where the following conditions (A) and (B) are satisfied, the composition is determined as being suitable as a screen foamer composition:

(A) before the treatment of (I) or (II) below, no micelle image is observed or a micelle image is hardly observed, and (B) after the treatment of (I) below, the micelle image is observed:

(I) the composition is allowed to stand in an open system, and (II) stress is applied to the composition.

According to this type of evaluation method, it is possible to determine whether or not the composition is suitable as a screen foamer composition, and thus a product exhibiting good bubbles can be provided by selecting a suitable composition. This evaluation method can be used only as it is or can be used in combination with the evaluation using the form of the low light transmission region of the foam as an index.

In a preferred embodiment of the present invention, the composition is determined as being more suitable as a screen foamer composition when the composition further satisfies the following condition (C):

(C) after the treatment of (II) above, the micelle image is more observed than before the treatment.

By using these criteria, more accurate evaluation can be conducted.

In a preferred embodiment of the present invention, in (C), as a particle size of the micelle image to be observed is smaller, the composition is determined as being more suitable as a screen foamer composition.

By using these criteria, more accurate evaluation can be conducted.

In a preferred embodiment of the present invention, in (C), as uniformity of a particle size of the micelle image to be observed is higher, the composition is determined as being more suitable as a screen foamer composition.

By using these criteria, more accurate evaluation can be conducted.

In a preferred embodiment of the present invention, the treatment of (II) is performed by applying stress to the composition by centrifugation.

By applying stress to the composition by centrifugation and then observing the composition by an optical microscope, it is possible to observe the micelle images more accurately and to determine more accurately whether or not the composition is suitable as a screen foamer composition.

Advantageous Effects of Invention

Since the foam of the present invention contains a non-ionic surfactant, the foam has high safety and is excellent in foam stability due to a new structure. The screen foamer composition of the present invention is preferable for forming the foam due to excellent foamability. Further, by using the evaluation method of the present invention, a composition capable of forming the foam can easily or accurately be evaluated.

According to the present invention as described above, it is possible to design and produce a novel foam-form preparation exhibiting good bubble which is applicable as an external preparation for skin not premised on being washed away.

DESCRIPTION OF EMBODIMENTS

Hereinafter, preferable embodiments will be described in the order of the foam of the present invention, the screen foamer composition for forming the foam, and the evaluation method for the composition.

<1> Foam of Present Invention

In the present invention, "foam" means bubbles as an aggregate and composed of an air layer and a bubble shell encapsulating the air layer.

<1-1> Structure of Foam

Figure 1:
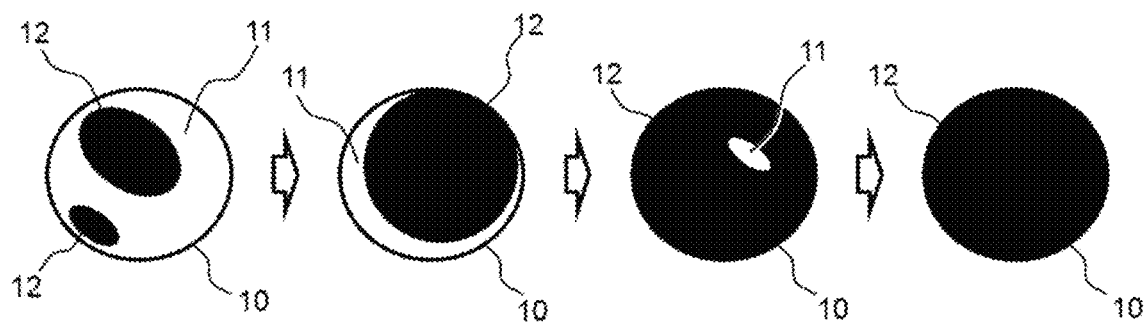
FIG. 1 schematically shows that when a foam 10 of the present invention is allowed to stand at 25° C., an area of a low light transmission region 12 occupying the surface area of the bubble shell expands over time so that the entire surface of the bubble shell becomes occupied by the low light transmission region 12.

The foam of the present invention will be described with reference to the figures. The foam 10 of the present invention contains a high light transmission region 11 and a low light transmission region 12 spreading across a surface of a bubble shell constituting the foam 10 (FIG. 1). The low light transmission region 12 has a lower light transmittance than the high light transmission region 11. Boundaries between the low light transmission region 12 and the high light transmission region 11 can be distinguished from each other due to a difference in light transmittance. It is preferable that the light transmittance in the low light transmission region 12 is substantially uniform.

It is preferable that the low light transmission region 12 has low light transmittance as it is observed by an optical microscope as gray or black.

When the foam 10 of the present invention is allowed to stand at 25° C., an area of the low light transmission region 12 occupying the surface area of the bubble shell expands over time. And finally, the entire surface of the foam 10 becomes occupied by the low light transmission region 12 (FIG. 1).

The foam of the present invention having the above-described characteristics has excellent foam stability.

In addition, in a process of expanding an area of the low light transmission region 12 occupying the surface area of the foam 10, more specifically, in a state in which the low light transmission region 12 occupies half or more than half of the surface area of the foam 10 when the foam 10 is allowed to stand at 25° C., as a difference between the maximum diameter and the minimum diameter of the high light transmission region 11 is smaller, the foam 10 has better foam stability.

Figure 2:
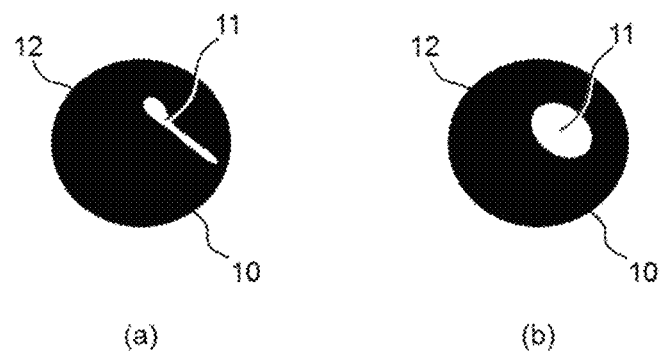
FIG. 2 schematically shows a difference in a shape of a high light transmission region 11 in a process of expanding an area of the low light transmission region 12 occupying the surface area of the bubble shell over time when the foam 10 is allowed to stand at 25° C.

For example, in the process of expanding the area of the low light transmission region 12, the foam 10 having the high light transmission region 11 having a small difference between the maximum diameter and the minimum diameter shown in FIG. 2(b) has excellent foam stability as compared with the foam 10 having the high light transmission region 11 having a large difference between the maximum diameter and the minimum diameter shown in FIG. 2(a).

Figure 3:
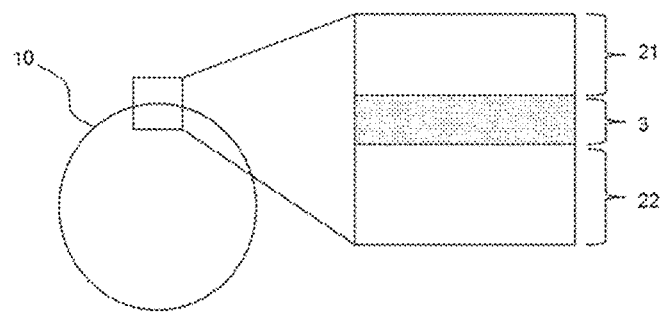
FIG. 3 schematically shows a cross-sectional view and an enlarged cross-sectional view of foam 10 containing a fatty acid soap as a conventional foam-forming ingredient.

For example, a foam containing a fatty acid soap as a foamable ingredient has a structure in which air is contained in one membrane with a double-layer structure arranged in such a manner that a hydrophilic portion of a fatty acid salt faces a liquid phase 3 and the hydrophobic portion thereof faces gas phases 21 and 22 (FIG. 3).

Figure 4:
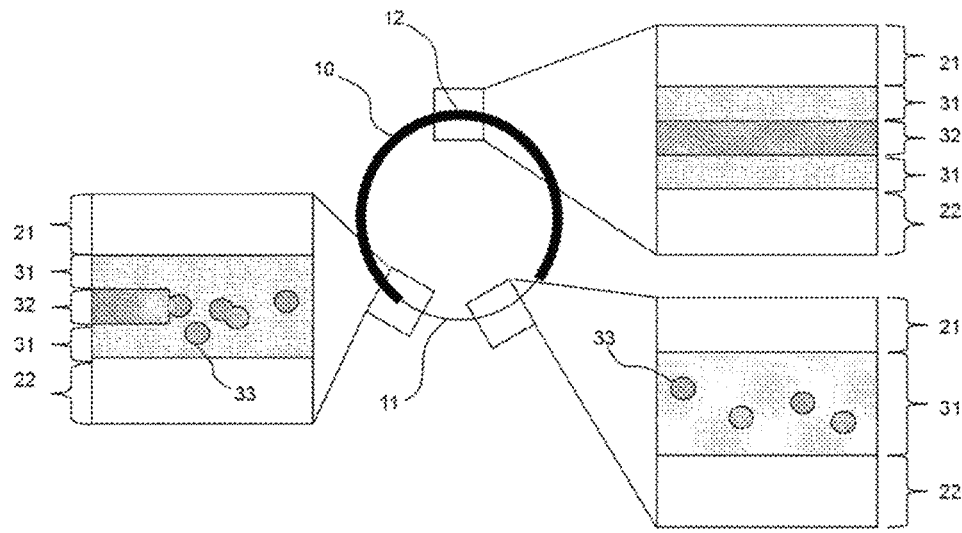
FIG. 4 schematically shows a cross-sectional view and an enlarged cross-sectional view of the foam 10 showing a process of expanding the low light transmission region 12 over time in the foam 10 of the present invention.

A structure of the bubble shell in the high light transmission region 11 in the foam of the present invention may also be a single layer structure composed of one aqueous ingredient phase 31 in which a non-ionic surfactant is arranged on a vapor-liquid interface (FIG. 4).

Further, the aqueous ingredient phase 31 preferably has a dispersion form of droplets (micelles) 33 containing a non-ionic surfactant, a polyhydric alcohol having a hydrophobic end and/or a polyhydric alcohol polymer.

Meanwhile, the structure of the bubble shell in the low light transmission region 12 is preferably a multiple structure. More specifically, the multilayer structure is preferably a two-phase three-layer structure. In other words, the structure of the bubble shell in the low light transmission region 12 preferably contains an aqueous ingredient phase 31 in contact with an outer gas phase 21 of the foam 10; an aqueous ingredient phase 31 in contact with an inner gas phase 22 of the foam 10; and a droplet phase 32 interposed between the two aqueous ingredient phases. In this case, the droplet phase 32 preferably contains a non-ionic surfactant, a polyhydric alcohol having a hydrophobic end and/or a polyhydric alcohol polymer.

Figure 5:
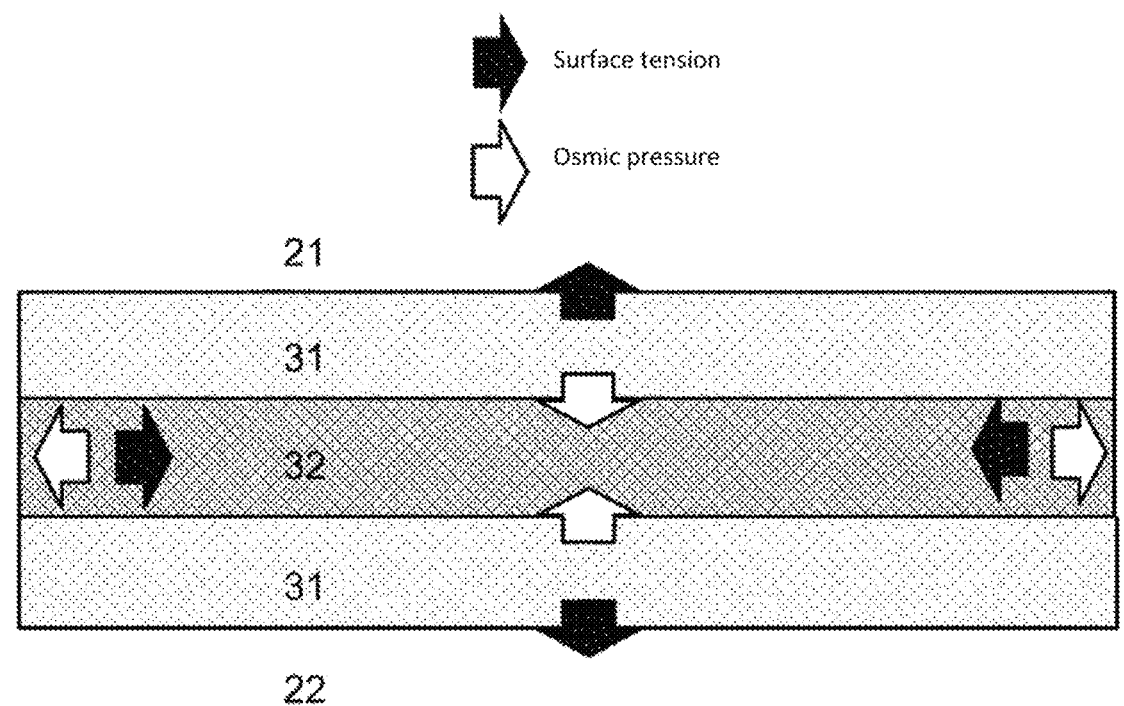
FIG. 5 schematically shows how a membrane of the foam 10 of the present invention spreads by antagonizing osmotic pressure and surface tension generated by an interlayer movement of polyhydric alcohol.

The foam 10 containing the fatty acid soap as a foam-forming ingredient shown in FIG. 3 forms a double-layer structure while remarkably reducing surface tension. In contrast, in the foam 10 of the present invention, the surface tension itself is not reduced, but the membrane is expanded by antagonizing the surface tension and an osmotic pressure generated by an interlayer movement of the polyhydric alcohol (see FIG. 5).

By forming a membrane having the structure described above, the foam can be formed without significantly reducing the surface tension. Therefore, it is possible to alleviate irritation to the skin due to remarkable reduction in surface tension. Therefore, the composition capable of forming the foam of the present invention is useful as a base material for external preparation of a usage form without the washing step.

<1-2> Ingredient of Foam

The foam of the present invention contains a non-ionic surfactant as an essential ingredient in the bubble shell. The non-ionic surfactant has a function of forming a foam.

The non-ionic surfactant can be applied without particular limitation as long as it forms a low light transmission region on the surface of the foam.

Further, an HLB value of the non-ionic surfactant is preferably 9 or more, more preferably 10 or more, further preferably 11 or more, and particularly preferably 13 or more. The HLB value of the non-ionic surfactant is, for example, 10 to 19.

The carbon number of the carbon chain constituting the hydrophobic group of the non-ionic surfactant is preferably 8 or more, more preferably 10 or more, and particularly preferably 12 or more. Further, the upper limit of the number of carbon atoms is preferably 22.

As the non-ionic surfactant, one or two or more selected from the following group X is preferably used.

(Group X)

Polyoxyethylene alkyl ether, polyoxyethylene alkenyl ether, polyoxyethylene hydrogenated castor oil, polyoxyethylene fatty acid ester, polyoxyethylene sorbitan fatty acid ester, polyoxyethylene fatty acid glyceryl, polyoxypropylene polyoxyethylene alkyl ether, and polyoxypropylene polyoxyethylene alkenyl ether.

Among them, a form containing a polyoxyethylene alkyl ether and/or a polyoxyethylene alkenyl ether is preferable as the non-ionic surfactant. Preferred forms of the present invention may contain, as the non-ionic surfactant, a form containing only polyoxyethylene alkyl ether and/or polyoxyethylene alkenyl ether, a form in combination with one or two or more selected from polyoxyethylene fatty acid ester, polyoxyethylene sorbitan fatty acid ester, and polyoxyethylene hydrogenated castor oil, as well as polyoxyethylene alkyl ether and/or polyoxyethylene alkenyl ether. Further, as the ingredient in combination of polyoxyethylene alkyl ether and/or polyoxyethylene alkenyl ether, polyoxyethylene fatty acid ester and/or polyoxyethylene hydrogenated castor oil are particularly preferable, and a combination of the polyoxyethylene fatty acid ester and polyoxyethylene hydrogenated castor oil may be preferable. In addition, a form in which only a polyoxyethylene sorbitan fatty acid ester is used as the non-ionic surfactant may also be preferable.

The number of carbon atoms of the alkyl or alkenyl constituting the polyoxyethylene alkyl ether or polyoxyethylene alkenyl ether is preferably 10 to 24, and more preferably 12 to 22.

Preferable examples of the polyoxyethylene alkyl ether or polyoxyethylene alkenyl ether may be polyoxyethylene oleyl ether, polyoxyethylene stearyl ether, polyoxyethylene lauryl ether, polyoxyethylene cetyl ether, polyoxyethylene behenyl ether, and the like.

Further, in the above polyoxyethylene alkyl ether or polyoxyethylene alkenyl ether, the average number of additional moles of polyoxyethylene is preferably 2 to 50, more preferably 4 to 45, further preferably 4 to 40, and particularly preferably 6 to 30.

The number of carbon atoms of the fatty acid constituting the polyoxyethylene fatty acid ester is preferably 8 to 24, and more preferably 12 to 18.

Preferable examples of the polyoxyethylene fatty acid ester may be saturated fatty acid esters and unsaturated fatty acid esters of polyoxyethylene such as polyoxyethylene oleate, polyoxyethylene stearate, polyoxyethylene laurate, or the like.

In addition, in the polyoxyethylene fatty acid ester, the average number of additional moles of polyoxyethylene is preferably 5 to 70. More preferably, the average number of additional moles of polyoxyethylene is 5 to 65. Still more preferably, the average number of additional moles of polyoxyethylene is 5 to 55.

The number of carbon atoms of the fatty acid constituting the polyoxyethylene sorbitan fatty acid ester is preferably 12 to 18.

Preferable examples of the polyoxyethylene sorbitan fatty acid ester may be monolauric acid polyoxyethylene sorbitan, monopalmitic acid polyoxyethylene sorbitan, monooleic acid polyoxyethylene sorbitan, monostearic acid polyoxyethylene sorbitan, trioleic acid polyoxyethylene sorbitan, tetraoleic acid polyoxyethylene sorbitan, and the like.

Further, in the polyoxyethylene sorbitan fatty acid ester, the average number of additional moles of polyoxyethylene is preferably 10 to 50, and more preferably 5 to 25.

In the polyoxyethylene hydrogenated castor oil, it is preferable that the average number of additional moles of polyoxyethylene is 30 to 90.

The carbon number of the alkyl or alkenyl constituting the polyoxypropylene polyoxyethylene alkyl ether or the polyoxypropylene polyoxyethylene alkenyl ether is preferably 16 to 24.

Preferable examples of polyoxypropylene polyoxyethylene alkyl ether or polyoxypropylene polyoxyethylene alkenyl ether may be polyoxypropylene polyoxyethylene cetyl and the like.

Further, the average number of additional moles of polyoxyethylene is preferably 2 to 30, and more preferably 4 to 20. Further, the average number of additional moles of polyoxypropylene is preferably 10 to 20, and more preferably 6 to 16.

Further, as a partial non-ionic surfactant, one or two or more from aliphatic alkanolamide type surfactants may be selected and contained in the composition.

The aliphatic alkanolamide type surfactant can be applied without particular limitation as long as it is used in conventional external preparations for skin such as external medicine, cosmetics, and the like. Specific examples thereof may be palm oil fatty acid monoethanolamide (cocamide MEA), palm oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), palm oil fatty acid methyl ethanolamide (cocamide methyl MEA), and the like. Palm oil fatty acid diethanolamide, lauric acid diethanolamide, and palmitic acid diethanolamide may be preferably exemplified.

The aliphatic alkanolamide type surfactant preferably has an amount of 1% by mass based on the total amount of the composition. More preferably, the aliphatic alkanolamide type surfactant has an amount of 0.5% by mass based on the total amount of the composition. Still more preferably, the aliphatic alkanolamide type surfactant is not contained at all.

The foam of the present invention may contain, in addition to the non-ionic surfactant having the HLB value of 9 or more, a non-ionic surfactant having an HLB value of 5 or less.

The non-ionic surfactant having the HLB value of 5 or less can be applied, without any particular requirement as long as it can be contained in an external preparation for skin, and the like.

Preferable examples of the non-ionic surfactant having the HLB value of 5 or less, may be glycerin fatty acid ester, sorbitan fatty acid ester, and the like.

Preferable examples of the glycerin fatty acid ester may include glyceryl monostearate and glyceryl monomyristate. The glyceryl monostearate is more preferable.

Preferable examples of the sorbitan fatty acid ester may be monostearic acid sorbitan, monooleic acid sorbitan, tristearic acid sorbitan, trioleic acid sorbitan, sesquistearic acid sorbitan, sesquioleic acid sorbitan, and the like. The monostearic acid sorbitan is more preferable.

Preferable examples of the combination of the non-ionic surfactant having the HLB of 9 or more and the non-ionic surfactant having an HLB value of 5 or less may be, as a non-ionic surfactant, a combination form of monostearic acid glycerin and/or monostearic acid sorbitan having an HLB of 5 or less with polyoxyethylene alkyl ether and/or polyoxyethylene alkenyl ether having an HLB of 9 or more; and a combination form of monostearic acid glycerin and/or monostearic acid sorbitan having an HLB value of 5 or less with one or two or more selected from polyoxyethylene fatty acid ester, polyoxyethylenated sorbitan fatty acid ester, and castor oil that may be polyoxyethylenated, which have an HLB of 9 or more, as well as polyoxyethylene alkyl ether and/or polyoxyethylene alkenyl ether having an HLB of 9 or more.

The foam of the present invention preferably contains an ionic surfactant (excluding phospholipids) in an amount of 1% by mass or less, and more preferably, the foam does not substantially contain the ionic surfactant. This allows the production of foam with high safety.

The foam of the present invention preferably contains an alcohol in the bubble shell. The alcohol in the foam of the present invention is a generic term of monohydric alcohol and polyhydric alcohol. These ingredients are preferably those having a property of mixing with water at an arbitrary ratio.

The alcohol in the foam of the present invention interacts with the non-ionic surfactant, thereby strengthening the bubble shell.

The alcohol in the foam of the present invention is preferably a polyhydric alcohol.

Preferable examples of the monohydric alcohol may be an alcohol having 1 to 3 carbon atoms. Ethanol, isopropyl alcohol and the like are more preferable.

The monohydric alcohol is preferably contained as a component of the aqueous ingredient phase in the above-described multilayer structure.

Preferable examples of the polyhydric alcohol may be a polyhydric alcohol having 2 to 6 carbon atoms in which hydroxyl groups are bonded to all the carbon atoms. Preferable examples of the polyhydric alcohol may be diethylene glycol, glycerol, erythritol, glucose, sorbitol, and the like.

It is preferable that the polyhydric alcohol having 2 to 6 carbon atoms in which hydroxyl groups are bonded to all the carbon atoms is contained as a component of the aqueous ingredient phase in the above-described multilayer structure.

Further, it is preferable to contain a polyhydric alcohol having a hydrophobic end. Preferable examples of the polyhydric alcohol having a hydrophobic end may be propylene glycol, 1,3-butanediol, 1,2-pentanediol, 1,2-hexanediol, hexylene glycol, and the like.

It is preferable that the polyhydric alcohol having a hydrophobic end is contained as a component of a droplet phase in the above-described multilayer structure.

Further, the polyhydric alcohol polymer also has the same action as that of the polyhydric alcohol having a hydrophobic end described above in the foam by association of hydrophilic groups with each other. Therefore, a form containing the polyhydric alcohol polymer is also preferable. As the polyhydric alcohol polymer, polypropylene glycol or polyethylene glycol can be preferably exemplified.

It is preferable that the polyhydric alcohol polymer is contained as a component of the droplet phase in the multilayer structure described above.

The polyhydric alcohol is preferably one or two or more selected from 1,3-butylene glycol, polyethylene glycol, glycerin and propylene glycol, and more preferably polyethylene glycol and 1,3-butylene glycol.

In addition, a molecular weight of the polyhydric alcohol is preferably 3500 or less, and more preferably 2000 or less.

The foam of the present invention preferably contains a polysaccharide which may be sulfated.

Examples of the polysaccharide which may be sulfated may be hyaluronic acids such as hyaluronic acid, hyaluronic acid derivatives, and the like, chondroitin sulfates such as chondroitin, and chondroitin sulfate, and the like, mucopolysaccharides such as dermatan sulfate, heparan sulfate, heparin, heparin-like substance, keratan sulfate, and the like, polyglucosamines such as chitin and chitosan, and the like; hydrophilic natural polymers such as xanthan gum, succinoglycan, carrageenan, guar gum, locust bean gum, galactan, Arabic gum, tragacanth gum, tamarind gum, agar, agarose, mannan, curdlan, pectin, alginic acid and salts thereof, starch, dextrin, celluloses, and the like; hydrophilic synthetic polymers such as starch derivatives such as carboxymethyl starch and salts thereof, acrylic acid grafted starch and salts thereof, or cellulose derivatives such as hydroxypropylcellulose and derivatives thereof, hydroxyethylcellulose and derivatives thereof, hydroxypropylmethylcellulose, hydroxypropylmethylcellulose derivatives such as hydroxypropylmethylcellulose phthalate, hydroxypropylmethylcellulose having a hydrocarbon group such as a stearyl group, and the like, sulfonated cellulose derivatives, carboxymethylcellulose and derivatives thereof and salts thereof, carboxymethylethylcellulose and salts thereof, cellulose acetate phthalate, cationized celluloses such as chlorinated O-[2-hydroxy-3-(trimethylammonio)propyl]hydroxyethyl cellulose (also referred to as "polyquaternium-10") and the like, ethylcellulose, croscarmellose and salts thereof, and the like.

These polysaccharides which may be sulfated may be preferably hyaluronic acids such as hyaluronic acid, hyaluronic acid derivatives, and the like, mucopolysaccharides such as dermatan sulfate, heparan sulfate, heparin, heparin-like substance, keratansulfate, and the like, polyglucosamines such as chitin, and chitosan, and the like. Particularly preferably, hyaluronic acid and a heparin-like substance can be exemplified.

The foam may contain only one kind of the polysaccharide which may be sulfated or a combination of two or more kinds thereof.

The polysaccharide which may be sulfated improves stabilization of dispersed droplets by being contained as a component of the aqueous ingredient phase in the multilayer structure described above. In addition, a moisturizing effect is also obtained as a secondary effect.

The foam of the present invention may contain an organic salt and/or an inorganic salt. In the foam of the present invention, a liquid property is adjusted with an organic salt and/or an inorganic salt, and excellent foamability, foam stability, and foam quality can be obtained without being affected by the liquid property in the range of strong acidity to strong alkaline (pH 2 to 12).

Examples of the organic salts and/or inorganic salts may be hydrochloric acid, citric acid, gluconic acid, succinic acid, acetic acid, tartaric acid, sorbic acid, lactic acid, maleic acid, sulfuric acid, phosphoric acid, malic acid, arginine, ammonia water, diisopropanolamine, diethanolamine, triisopropanolamine, triethanolamine, monoethanolamine, potassium hydroxide, calcium hydroxide, and sodium hydroxide, or salts thereof, but the organic salts and/or inorganic salts are not limited thereto.

The foam of the present invention may contain an optional ingredient used in a composition for external use such as external medicine for skin, cosmetics, and the like.

Preferable examples of the optional ingredients may be hydrocarbons such as liquid paraffin, squalane, and the like, esters such as jojoba oil, dodecanoic acid oleyl ester, cetyl isooctanate, and the like, N-alkyl-2-pyrrolidone such as N-methyl-2-pyrrolidone, N-ethyl-2-pyrrolidone, and the like, alkylene carbonate having 2 to 4 carbon atoms such as ethylene carbonate, propylene carbonate, and the like, crotamiton, triethyl citrate, ethyl ether of diethylene glycol, triacetin, diesters of dibasic acids having 5 to 12 carbon atoms such as diisopropyl adipate, diethyl adipate, diisopropyl sebacate, and the like, solvents such as benzyl alcohol, and the like, fatty acids such as oleic acid, isostearic acid, and the like, thickeners such as carboxyvinyl polymer, xanthan gum, and the like, disinfectants such as parabens and chlorhexidine gluconate, and the like. Among these optional ingredients, preferable ingredients may be appropriately selected and contained.

By containing the active ingredient in the foam of the present invention, the foam can be used as a medicament in a foam formulation. Preferable examples of the active ingredient may be steroids such as hydrocortisone, clobetasone, dexamethasone, and betamethone, derivatives thereof, and the like, non-steroidal anti-inflammatory agents such as indomethacin, suprofen, and the like, disinfectants such as chlorhexidine gluconate, benzalkonium chloride, and the like, antifungal agents such as terbinafine, butenafine, bifonazole, ketoconazole, and the like, antibiotics such as penicillin, methicillin, tetracycline, colistin methanesulfonic acid, phosphomycin, and the like, antipruritic agents such as nalfurafine, and the like, immunosuppressants such as vitamin A, vitamin B, vitamin C, vitamin D, vitamin E, and tacrolimus, and the like.

In addition, the present invention may contain a form containing an antifungal agent such as a naphthylamine-based, benzylamine-based, azole-based or dithiolane-based antifungal agent, as a preferable example of the antifungal agent.

The active ingredient may also be contained in the bubble shell in any one region of the low light transmission region and the high light transmission region, depending on the solubility in water. In addition, the above active ingredient may be contained as anyone ingredient of the aqueous ingredient phase and the droplet phase in the above-described multilayer structure.

As the solvent, for example, it is preferable to contain a polar solvent selected from Group Y below.

(Group Y)

N-alkylpyrrolidone, alkylene carbonate, benzyl alcohol, adipic acid diester, and sebacic acid diester The polar solvent of the Group Y is excellent in the solubility of a poorly soluble drug (active ingredient) and the poorly soluble drug can stably be contained in the foam of the present invention.

A preferable example of the N-alkylpyrrolidone may be N-alkyl-2-pyrrolidone containing an alkyl chain having 1 to 4 carbon atoms. More preferably, the N-alkylpyrrolidone is N-methyl-2-pyrrolidone or N-ethyl-2-pyrrolidone.

As the alkylene carbonate, propylene carbonate is preferable.

As the adipic acid diester, diethyl adipate, and diisopropyl adipate are preferable.

As the sebacic acid diester, diethyl sebacate, and diisopropyl sebacate are preferable.

The polar solvent may be contained in the composition alone, or may be contained in the composition by selecting one or two or more kinds of the polar solvents.

The foam of the present invention preferably contains a phospholipid. The phospholipid may be applied without particular limitation as long as the phospholipid is used as conventional external preparations for skin such as external medicine, cosmetics, and the like. Specifically, preferable examples of the phospholipid may be lecithin refined from soybeans or yolk, phosphatidylcholine which is a main ingredient of lecithin, hydroxylated lecithin, phosphatidylic acid which is a main chain of phosphatidylcholine, hydrogenated lecithin, phosphatidylserine, phosphatidylinositol, phosphatidylethanolamine, phosphatidylglycerol, sphingomyelin, cerebroside, lysomers thereof, and the like. More preferably, the phospholipid is lecithin and hydrogenated lecithin.

The phospholipid eliminates bubbles within a suitable time after application without lowering the foamability in addition to an action to improve bubble quality of the composition and an excellent moisturizing action, and thus the composition has low irritation, is easy to spread, and does not leave bubbles at the time of application and spreading, which is appropriate for application to skin with reduced skin barrier function such as atopic dermatitis or the like. As the phospholipid, one kind may be used simply or a combination of two or more kinds may be used.

The foam of the present invention may contain not only the phospholipid but also sebum ingredients such as squalene, cholesterol, cholesterol ester, wax ester, triglyceride, diglyceride, monoglyceride, ceramide, free fatty acid, and the like, amino acids such as serine, glycine, and the like, natural moisturizing factors such as pyrrolidonecarboxylic acid and salts thereof, urea, lactic acid, and the like, acidic mucopolysaccharides such as hyaluronic acid, and the like.

The foam of the present invention may contain one or more kinds selected from an aminocarboxylic acid derivative and a salt thereof, a phosphonic acid derivative and a salt thereof, a phenanthroline derivative and a salt thereof, a phytic acid derivative and a salt thereof, and a gluconic acid derivative and a salt thereof.

Preferable examples of the amino acid carboxylic acid derivative may be ethylenediamine tetraacetic acid, nitrilotriacetic acid, diethylenetriamine pentaacetic acid, hydroxyethylethylenediamine triacetic acid, triethylenetetramine hexaacetic acid, 1,3-propanediamine tetraacetic acid, 1,3-diamino-2-hydroxypropane tetraacetic acid, hydroxyethylimino diacetic acid, dihydroxyethylglycine, glycol ether diamine tetraacetic acid, dicarboxymethylglutamic acid, (S,S)-ethylenediamine succinic acid, salts thereof, and the like. More preferably, ethylenediamine tetraacetic acid, and salts thereof.

Preferable examples of the phosphonic acid derivative may be hydroxyethylidene diphosphonic acid, nitrilotris (methylenephosphonic acid), phosphonobutanetricarboxylic acid, ethylenediamine tetra (methylenephosphonic acid), salts thereof, and the like. More preferably, hydroxyethylidene diphosphonic acid and a salt thereof.

Preferable compositions such as the content of each ingredient described above are described in the section <2> Screen foamer composition of the present invention, and the composition is also applied to the foam of the present invention.

<1-3> Usage of Foam

Since the foam of the present invention is very safe and has foam stability, the foam can be uniformly applied without burdening the affected part.

From these properties, the foam of the present invention is preferably used as a medicament containing an active ingredient for skin diseases. In this case, the foam is used without being removed after application.

<1-4> Preparation Method for Foam

The foam of the present invention can be prepared by passing the screen foamer composition described in the following section through a screen foamer.

Here, the screen foamer means a mechanism for pressing a liquid to pass through a net type screen, thereby mixing the composition with air to achieve foaming. A pump foamer, a tube foamer, and the like, are known, and particularly, a pump foamer may be preferably exemplified. The pump foamer is a device that discharges contents that are pumped by a pump, in the form of a foam. A container equipped with the screen foamer is well known (see, for example, JP 2012-45525 A and JP 2008-307478A), and a commercially available container is also available, and thus these containers can be used appropriately.

Hereinafter, the screen foamer composition is described in detail.

<2> Screen Foamer Composition of Present Invention

The screen foamer composition of the present invention (hereinafter, the composition of the present invention) is a composition used for the preparation of the foam of the present invention described above.

<2-1> Ingredients of Composition

Hereinafter, the ingredients of the composition of the present invention are described. In addition, as to preferable forms of the ingredients, the description of the section <1> Foam of the present invention is applied.

The composition of the present invention contains, as a foam forming agent, a non-ionic surfactant. In other words, in the composition of the present invention, ingredients capable of forming a foam (typically, an ionic surfactant), which are other than the non-ionic surfactant, are not contained in forms in which foamability is exhibited. For example, the content of the ionic surfactant (provided that excluding phospholipids) is preferably 1% by mass or less, and more preferably, the ionic surfactant is not substantially contained.

In the composition of the present invention, the non-ionic surfactant is blended in such an amount that the composition is in a solubilized state.

For example, the non-ionic surfactant is preferably contained in an amount of 1 to 15% by mass based on the total amount of the composition. Further, the non-ionic surfactant is contained in an amount of preferably 2 to 12% by mass, more preferably 2 to 10% by mass, further preferably 2.5 to 10% by mass, and particularly preferably 2.5 to 7% by mass, based on the total amount of the composition. A proportion of the non-ionic surfactant having the predetermined HLB value is preferably 80% by mass or more, more preferably 90% by mass or more, and particularly preferably 95% by mass or more, based on the total amount of the non-ionic surfactant. For example, it is also preferable that the total amount of the non-ionic surfactant is composed of a non-ionic surfactant having an HLB value of 9 or more, preferably 10 or more, more preferably 11 or more, and particularly preferably 13 or more.

The proportion of the non-ionic surfactant selected from the group X is preferably 80% by mass or more, more preferably 90% by mass or more, and particularly preferably 95% by mass or more, based on the total amount of the non-ionic surfactant. For example, it is also preferable that the total amount of the non-ionic surfactant is composed of the non-ionic surfactant selected from the group X.

Further, a proportion of the polyoxyethylene alkyl ether and/or the polyoxyethylene alkenyl ether is preferably 25% by mass or more, more preferably 40% by mass or more, further preferably 50% by mass or more based on the total amount of the non-ionic surfactant. The upper limit of this proportion is not particularly limited, but may be, for example, 90% by mass or less, preferably 80% by mass or less.

When not only polyoxyethylene alkyl ether and/or polyoxyethylene alkenyl ether but also other non-ionic surfactants are contained as the non-ionic surfactant, the ratio of the total content of polyoxyethylene alkyl ether and/or polyoxyethylene alkenyl ether to the total content of non-ionic surfactants other than polyoxyethylene alkyl ether and/or polyoxyethylene alkenyl ether, is preferably 1:5 to 5:1, more preferably 1:4 to 4:1, and further preferably 1:3 to 3:1, by a mass ratio.

In the composition of the present invention, when the aliphatic alkanolamide type surfactant is used, for example, an amount of the aliphatic alkanolamide type surfactant is 0.5 to 10% by mass, and preferably 1 to 5% by mass.

In the composition of the present invention, when the non-ionic surfactant having an HLB value of 5 or less is combined with the non-ionic surfactant having an HLB value of 9 or more, a mass ratio thereof is preferably 1:3 to 3:1, and more preferably 1:2 to 2:1.

Further, when the non-ionic surfactant having an HLB value of 9 or more is blended together with the non-ionic surfactant having an HLB value of 5 or less, a weighted average of HLB values is preferably 9 to 16.

The content of the monohydric alcohol is preferably 5 to 25% by mass, more preferably 10 to 20% by mass, and further preferably 10 to 15% by mass based on the total amount of the composition.

The content of the polyhydric alcohol having 2 to 6 carbon atoms in which hydroxyl groups are bonded to all the carbon atoms is preferably 0.001 to 40% by mass, more preferably 0.001 to 30% by mass, and further preferably 1 to 30% by mass.

In the case of containing both a monohydric alcohol and a polyhydric alcohol having 2 to 6 carbon atoms in which hydroxyl groups are bonded to all the carbon atoms, the total amount is preferably 10 to 45% by mass, and more preferably 20 to 40% by mass.

The content of the polyhydric alcohol having a hydrophobic end and the polyhydric alcohol polymer is preferably 1 to 40% by mass, more preferably 5 to 30% by mass, and further preferably 10 to 20% by mass, based on the total amount of the composition. By setting the content within this concentration range, it is possible to provide a composition capable of forming a foam having a stable bubble shell.

The content of the polyhydric alcohol having 2 to 6 carbon atoms in which hydroxyl groups are bonded to all the carbon atoms, the polyhydric alcohol having a hydrophobic end and the polyhydric alcohol polymer is, in the total amount, preferably 10 to 60% by mass, and more preferably 12 to 50% by mass, based on the total amount of the composition.

The total content of the alcohol is preferably 10 to 50% by mass, more preferably 12 to 45% by mass, and particularly preferably 15 to 30% by mass, based on the total amount of the composition. Further, the composition of the present invention preferably contains the polyhydric alcohol in an amount of 10% by mass or more, and more preferably 10 to 45% by mass, based on the total content of the alcohols.

By using the alcohol within the above-described range of content, the composition of the present invention can keep the discharged foam for a long time and can further improve the feeling of use such as moisturizing feeling or the like.

In addition, the following preferred forms of the composition of the present invention are described:
a form containing 1,3-butylene glycol in an amount of 5 to 30% by mass, and more preferably 10 to 25% by mass; and
a form containing not only the 1,3-butylene glycol but also other polyhydric alcohols.

By containing the above-described alcohol, particularly, the polyhydric alcohol at a high concentration, it is possible to form bubbles having a bubble shell in which an interface with air is strengthened by interaction with the non-ionic surfactant. Further, by containing alcohol at a high concentration, a composition capable of implementing a moisturizing feeling can be obtained.

The foam of the present invention preferably contains a polysaccharide which may be sulfated. In this case, the content of the polysaccharide is preferably 0.001 to 5% by mass, and more preferably 0.01 to 1% by mass.

In the composition of the present invention, when the polar solvent is contained, the content thereof is preferably 1 to 30% by mass, more preferably 1 to 15% by mass, and further preferably 1 to 10% by mass, based on the total amount of the composition.

In addition, in the composition of the present invention, the content of the polar solvent is preferably 20 to 250 times by mass, and more preferably 30 to 200 times by mass, of the content of the poorly soluble drug (active ingredient).

In the composition of the present invention, by setting the concentration of the polar solvent within the above range, the strength of the discharged foam can be increased, and the active ingredient can be stably blended into the composition.

Further, by setting the concentration of the polar solvent within the above range, the composition of the present invention can reduce a feeling of irritation upon application and spreading.

The composition of the present invention may contain an organic salt and/or an inorganic salt. In the composition of the present invention, a liquid property is adjusted with an organic salt and/or an inorganic salt, and excellent foamability, foam stability, and foam quality can be formed without being affected by the liquid property in the range of strong acidity to strong alkaline (pH 2 to 12). As to preferable forms of the organic salt and/or the inorganic salt, the description of the section <1> Foam of the present invention is applied.

In the composition of the present invention, when the organic salt and/or the inorganic salt are contained, the content thereof is preferably such that the liquid property of the composition is adjusted to the above pH range (pH 2 to 12). The content varies depending on the type of organic salt and/or inorganic salt, but is generally 0.1 to 10% by mass, and preferably 0.5 to 5% by mass, based on the total amount of the composition.

The composition of the present invention can be applied to detergents and the like, in the case of alkalinity, and the composition can be applied to pharmaceuticals, cosmetics, and the like, which reduce irritation on the skin, in the case of weak acidity. Particularly, regarding the weak acidity, it is preferable for applying the composition to pharmaceuticals or cosmetics used in a form that is not removed after application.

In the composition of the present invention, when the phospholipid is contained, the content of the phospholipid is preferably 0.001 to 10% by mass based on the total amount of the composition. More preferably, the content of the phospholipid is 0.01 to 5% by mass.

By setting the concentration of the phospholipid within the above range in the composition of the present invention, it is possible to prevent changes in properties of the foam due to the effect of pH while simultaneously increasing strength of the discharged foam. Further, it is possible to avoid irritation to the skin while simultaneously improving the feeling of use at the time of application and spreading.

When the composition of the present invention contains one or two or more selected from an aminocarboxylic acid derivative and a salt thereof, a phosphonic acid derivative and a salt thereof, a phenanthroline derivative and a salt thereof, a phytic acid derivative and a salt thereof, a gluconic acid derivative and a salt thereof, the derivative and the salt thereof preferably have a content of 0.0001 to 10% by mass, and more preferably 0.001 to 5% by mass, based on the total amount of the composition.

By setting the content of the derivative or the salt thereof within the above range, the composition of the present invention can inhibit decomposition, denaturation, and the like, of the active ingredient or the pharmaceutical ingredient and improve the preparation stability.

The preferable content of the optional ingredients other than the above-described components varies depending on the purpose of blending, but is preferably about 0.1 to 20% by mass.

It is preferable that in the composition of the present invention, the use of the following ingredients is limited from the viewpoints of safety, in particular, from the viewpoint that the composition should not contain compositions exhibiting irritation or the feeling of irritation for a person having sensitive skin.

The total content of the ionic surfactant excluding the phospholipid is preferably 1% by mass or less, and it is preferable that the ionic surfactant is not substantially contained.

Further, it is preferred that the use of the alkanolamide type surfactant among the non-ionic surfactants is also limited, and in a particularly preferred form, the alkanolamide type surfactant is not substantially contained. In addition, it is preferred that the use of polyoxyethylene polyoxypropylene glycol among the non-ionic surfactants is limited since anaphylaxis is caused in a mucous membrane. The amount of these non-ionic surfactants to be used is preferably 20% by mass or less, more preferably 10% by mass or less, and further preferably 5% by mass or less, as a proportion of the nonionic surfactant. In particular, it is preferred that the non-ionic surfactant is not contained.

Further, it is preferable that silicone is not substantially contained.

<2-2> Physical Properties of Composition

The composition of the present invention preferably contains the above-described ingredients and is in a solubilized state, and more preferably has a microemulsion formulation. Whether or not the composition has the microemulsion formulation can be confirmed as follows.

(1) Immediately after preparation, micelles are not confirmed even when observed by a microscope at a magnification of 100 to 1000 times.

(2) When stress is applied to the composition by centrifugation, or the like, and the composition is observed by a microscope at a magnification of 100 to 1000 times, the presence of micelles (average particle size of 1 to 10 microns) can be confirmed. Here, preferred conditions for the centrifugation may be, for example, 1000 to 100000 g for 1 to 5 minutes, and the like.

(3) When dropped onto a slide glass and left at room temperature for 1 hour, the micelles are hardly observed or the micelles are observed clearly.

The composition of the present invention is preferably an oil in water (O/W) type microemulsion. In this form, when the composition contains an alcohol, preferably a polyhydric alcohol, the composition preferably has an oil in water (O/W) type of (alcohol+non-ionic surfactant)/(water+alcohol).

When the composition has the microemulsion formulation, it is preferable to have a form obtained by dispersing dispersed droplets containing the non-ionic surfactant and the polyhydric alcohol having a hydrophobic portion in a continuous phase. The dispersion form generally has a microemulsion form, and by applying stress to a system such as by centrifugation or the like, micromicelles are combined to form micelles, which are then converted into general solubilized state or emulsified state. By the above-described method, it can be confirmed that the composition is a microemulsion.

Further, when the composition has the microemulsion formulation, the continuous phase preferably contains a mono-alcohol having 1 to 3 carbon atoms, a polyhydric alcohol having 2 to 6 carbon atoms in which hydroxyl groups are bonded to all the carbon atoms, a polysaccharide which may be sulfated, and the like, while containing water as a main ingredient.

The composition of the present invention generates bubbles bypassing the composition through a screen foamer. In addition, the foam after foaming is persistent. Further, in the preferred form of the composition of the present invention, stability in long-term preservation is excellent without precipitating crystals, and the like.

The composition of the present invention is preferably aqueous. Here, the aqueous indicates that water is contained to the extent that water functions as a base. For example, the content thereof is 15% by mass or more, preferably 20% by mass or more, and more preferably 30% by mass or more.

The composition of the present invention contains water in an amount of preferably 40 to 85% by mass, more preferably 50 to 80% by mass, and further preferably 55 to 75% by mass.

In the composition of the present invention, water is an important ingredient for forming a foam when discharged through a screen foamer.

By setting the amount of water within the above range, the composition of the present invention can form excellent foam with excellent foamability and foam stability. In addition, in order to stably maintain the bubble during the application for external use, it is effective to set the amount of water within the above range.

Further, the composition of the present invention satisfies the following condition (A). Preferably, the following (A) and (B) are satisfied. More preferably, the following conditions (A), (B) and (C) are satisfied.

(A) before the treatment of (I) or (II) below, no micelle image is observed or a micelle image is hardly observed, and (B) after the treatment of (I) below, the micelle image is observed:

(C) after the treatment of (II) below, the micelle image is more observed than before the treatment:

(I) the composition is allowed to stand, and (II) stress is applied to the composition.

In the screen foamer composition conforming to these conditions, the foam formed by filling in a screen foamer container has the following characteristics.

(1) It is possible to obtain the foam of the present invention, i.e, a foam in which the entire surface of the bubble shell becomes occupied by the low light transmission region under the condition in which the composition is allowed to stand at 25° C.

(2) The bubble shell in the low light transmission region is formed by combining the micelles.

(3) The surface tension of the composition itself is not lowered much.

The treatment of (I) is, for example, a treatment in which the composition is allowed to stand in an open system. The treatment of (I) is preferably a treatment in which the composition is allowed to stand for 1 hour in an open system. In the composition, a case where it is confirmed that the micelles are clearly confirmed when left on a slide glass for 1 hour is preferred as the composition of the present invention as compared with a case where the micelles are not confirmed. This is because it is an index indicating the ease of movement of the polyhydric alcohol between phases.

Further, preferred examples of the treatment (II) of applying the stress in the composition of the present invention may be treatment of applying the stress by tensile stress, compressive stress, centrifugation, and the like. Among them, the treatment of (II) is preferably a treatment for applying stress by centrifugal separation. Conditions for centrifugation may be, for example, 10000 to 20000 g for 1 to 5 minutes.

In addition, the observation of the micelle phase is preferably performed by observation by an optical microscope at a magnification of 100 to 5000 times. The observation magnification is preferably 100 to 2000 times, and more preferably 100 to 1000 times. Further preferably, the observation magnification is 100 to 400 times.

Upon definition of the preferred form of the composition of the present invention, it is important whether or not the micelles can be observed after applying an over-time condition such as being allowed to stand in an open system or the like, or a stress loading condition.

The composition of the present invention is preferably in the form of a composition for external use to the skin, such as an external medicine for skin, a cosmetic, or the like. More preferably, it is intended to be used as an embodiment not to be removed after application.

<2-3> Preparation Method for Composition

The composition of the present invention can be produced by solubilizing the above-described ingredients at room temperature or higher. The composition of the present invention is preferably prepared by solubilizing the above-described ingredients at 50° C. or higher, and more preferably by solubilizing the ingredients at or above the cloud point of the non-ionic surfactant.

The composition of the present invention can be prepared by solubilization around room temperature, but it is possible to prepare a composition more suitable as a screen foamer composition by solubilizing the ingredients at or above the non-ionic surface surfactant.

<3> Evaluation Method for Screen Foamer Composition of the Present Invention

Hereinafter, an evaluation method for a screen foamer composition according to the present invention (hereinafter referred to as an evaluation method of the present invention) is described, but the definitions of the terms in the description, and the like, can be applied to the description of the above <1> and <2>.

The evaluation method of the present invention is performed by observing an appearance of the surface of the bubble shell when the screen foamer composition containing the non-ionic surfactant as a foam forming agent is passed through a screen foamer to form a foam.

That is, when the high light transmission region and the low light transmission region are observed on the surface of the bubble shell of the formed foam, and in a case where it is confirmed that when the foam is allowed to stand at 25° C., an area of the low light transmission region occupying the surface area of the bubble shell expands over time so that the entire surface of the bubble shell becomes occupied by the low light transmission region, the composition is determined as being more suitable as a screen foamer composition.

Meanwhile, in a case where it is not confirmed that when the foam is allowed to stand at 25° C., and that an area of the low light transmission region occupying the surface area of the bubble shell expands over time so that the entire surface of the bubble shell becomes occupied by the low light transmission region, the foam is determined as being unsuitable as a screen foamer composition.

In other words, in the evaluation method of the present invention, when the foam is formed from the screen foamer composition and in a case where a change in the embodiment shown in FIG. 1 is observed on the surface of the foam, the composition is determined as being suitable as a screen foamer composition.

The foamability and the foam stability of the bubble of foam formed by the screen foamer composition may differ depending on the preparation method, the preparation order, and the like.

In the evaluation method of the present invention, the difference in the foamability and the foam stability resulting from the differences in the preparation method and the preparation order can be determined by the change of the embodiment of the low light transmission region on the surface of the foam.

The evaluation method of the present invention is not particularly limited to a method for observing the low light transmission region and the high light transmission region formed on the surface of the foam. For example, the evaluation method may include observation with an optical microscope or an electron microscope, identification of the structure by X-ray diffraction, and the like. The evaluation method of the present invention is performed, in view of simplicity and accuracy, preferably, by a microscope, and more preferably by an optical microscope.

Further, in the evaluation method of the present invention, the composition can be determined as being more suitable as a screen foamer composition as a difference between the maximum diameter and the minimum diameter of the high light transmission region is smaller, which is observed in a process of expanding an area of the low light transmission region occupying the surface area of the bubble shell over time, and more specifically, in a state in which the low light transmission region occupies half or more than half of the surface area of the foam when the foam is allowed to stand at 25° C.

For example, in the process of expanding the area of the low light transmission region 12, a case of observing a high light transmission region 11 having a small difference between the maximum diameter and the minimum diameter shown in FIG. 2(b) can be determined as being more suitable as a screen foamer composition as compared to a case of observing a high light transmission region 11 having a large difference between the maximum diameter and the minimum diameter shown in FIG. 2(a).

Further, in the evaluation method of the present invention, when the composition containing the non-ionic surfactant is observed by an optical microscope without passing through the screen foamer, and in a case where the following condition (A) is satisfied, the composition is determined as being suitable as a composition for a screen foamer.

Preferably, when the conditions (A) and (B) are satisfied, the composition is determined as being suitable as a composition for a screen foamer.

More preferably, when the conditions (A), (B), and (C) are satisfied, the composition is determined as being suitable as a composition for a screen foamer:

(A) before the treatment of (I) or (II) below, no micelle image is observed or a micelle image is hardly observed, and (B) after the treatment of (I) below, the micelle image is observed, (C) after the treatment of (II) below, the micelle image is more observed than before the treatment:

(I) the composition is allowed to stand, and (II) stress is applied to the composition.

Preferable forms of respective treatments, observation methods, and conditions are the same as described above.

The evaluation method may be used alone as an evaluation method for the composition. Further, the evaluation method may be used in combination with evaluation regarding the low light transmission region of the foam described above.

Hereinafter, the present invention is described in more detail with reference to Examples.

Example 1

Compositions 1 to 3 were prepared according to the following Table 1. That is, from the heparin-like substance, which is a prescription ingredient, to the POE-hydrogenated castor oil 60 were weighed respectively, dissolved by heating at 80° C., stirred and cooled to room temperature, and remaining ingredients were added thereto, followed by stirring to obtain Compositions 1 to 3. In addition, Compositions 1 to 3 were tested according to the following Test Examples 1 to 3.

TABLE 1

| Name of components | Composition 1 | Composition 2 | Composition 3 |
|---|---|---|---|
| Heparin-like substance | 0.3 | 0 | 0.3 |
| 1,3-buthylene glycol | 15 | 15 | 5 |
| JP glycerin 85-S | 25 | 25 | 35 |
| Lauromacrogol (BL-9EX) | 1.5 | 1.5 | 1.5 |
| Polyethylene glycol monostearate (MYS-40MV) | 1 | 1 | 1 |
| POE-hydrogenated caster oil 60 (HCO-60) | 1 | 1 | 1 |
| D-sorbitol | 0.5 | 0.5 | 0.5 |
| Purified sodium hyaluronate | 0.025 | 0.025 | 0.025 |
| Methyl parahydroxybenzoate | 0.2 | 0.2 | 0.2 |
| Sodium citrate | 0.4 | 0.4 | 0.4 |
| Citric acid hydrate | 0.03 | 0.03 | 0.03 |
| Purified water | 55.045 | 55.345 | 55.045 |
| | | | (% by mass) |

<Test Example 1> Observation of Foam

Figures 6, 7:
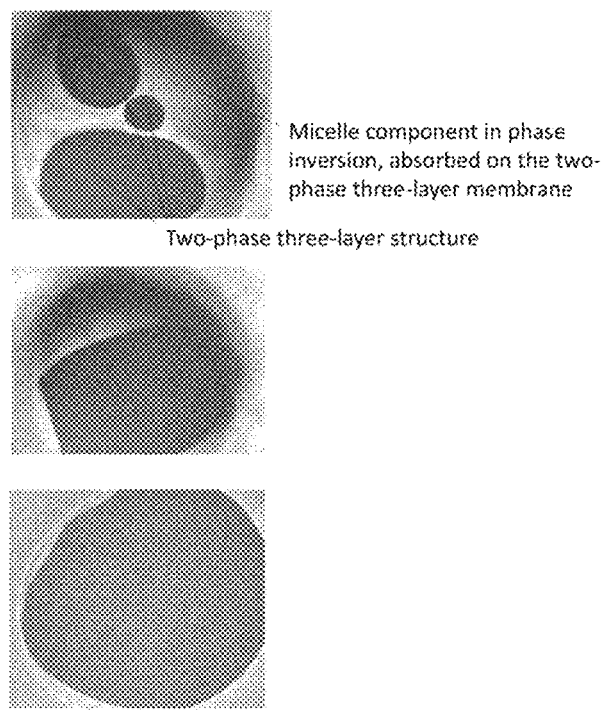
FIG. 6 shows results of Test Examples 1 to 3.
FIG. 7 shows a change in foam morphology over time of Composition 1 in Test Example 1, showing a time lapse of the changes from top to bottom.

Compositions 1 to 3 were passed through a pump foamer to form foam. The foam was placed on a slide glass and observed by an optical microscope to evaluate foamability and foam stability. Further, it was observed whether or not the high light transmission region having high light transmittance and the low light transmission region having low light transmittance were formed on the surface of the foam, and any changes of the embodiments thereof were observed. Results thereof are shown in FIG. 6. FIG. 6 also shows an image of the foam placed on the slide glass. In addition, FIG. 7 shows an image showing the change over time with respect to Composition 1.

In addition, foamability and foam stability of the foam formed from each composition were evaluated.

<Test Example 2> Observation of Composition After Being Allowed to Stand in an Open System The above compositions 1 to 3 were put on a slide glass immediately after preparation and observed by a microscope. In addition, after being allowed to stand on the slide glass for 1 hour, the composition was observed by an optical microscope. Confirmation whether or not the micelles were formed was evaluated by optical microscope observation immediately after the preparation and after being allowed to stand for 1 hour in the atmosphere, respectively. Results thereof are shown in FIG. 6.

<Test Example 3> Observation of Composition After Centrifugation

Compositions 1 to 3 were each placed in a polyethylene centrifuge tube in an amount of 100 µl, followed by centrifugation (15000 g, 1 minute). After centrifugation, Compositions 1 to 3 were each placed on a slide glass and observed by an optical microscope, and the observed micelles were evaluated. Results thereof are shown in FIG. 6.

As a result of Test Example 1, it was confirmed that the low light transmission region and the high light transmission region were present on the foam surface thereof immediately after the formation of the foam, and the ratio of the low light transmission region occupying on the foam surface gradually increased, and finally, it could be observed that the entire surface of the foam was composed of the low light transmission region (FIGS. 6 and 7).

Further, as to the shape of the high light transmission region observed in the process of expanding the low light transmission region, an island-like high light transmission region having a small difference between the minimum diameter and the maximum diameter was observed in Composition 1, while an elongated high light transmission region having a large difference between the minimum diameter and the maximum diameter was observed in Composition 3 (FIG. 6).

The foam formed from the Compositions 1 to 3 were all excellent in foamability and foam stability. In addition, the foamability and the foam stability were good in the order of Composition 1>Composition 2>Composition 3. In other words, it could be appreciated that Composition 1 formed a good foam, the Composition 1 containing 15% by mass of 1,3-butylene glycol (1,3 BG), which is a polyhydric alcohol having a hydrophobic end group, and 0.3% of the heparin derivative.

The results of Test Example 1 show the foam in which the high light transmission region and the low light transmission region were formed, and when the foam is allowed to stand at 25° C., an area of the low light transmission region occupying the surface area of the bubble shell expands over time so that the entire surface of the bubble shell becomes occupied by the low light transmission region, which had excellent foamability and foam stability.

In addition, when observing an island-shaped high light transmission region having a small difference between the minimum diameter and the maximum diameter with respect to the shape of the high light transmission region observed in the process of expanding the low light transmission region, it could be appreciated that the foam had better properties.

From the results of Test Example 2, it could be appreciated that no micelles were observed in Compositions 1 to 3 in the microscopic observation immediately after preparation. Further, after being allowed to stand for 1 hour in the atmosphere, micelles were observed in Compositions 1 to 3. The number of micelles was higher in the order of Composition 1>Composition 3>Composition 2.

From the results of Test Example 3, the micelles were confirmed in all of Compositions 1 to 3 by microscopic observation after centrifugation (15000 g, 1 minute). The number of micelles was higher in the order of Composition 2>Composition 1> Composition 3.

In addition, the size of micelles was larger in the order of Composition 3>Composition 2>Composition 1. The uniformity of the micelles was higher in the order of Composition 1>Composition 2>Composition 3. When combining this result and the results of Test Example 1, as the diameter of the micelle appearing after centrifugation is smaller, the composition can be determined as a composition capable of forming high quality foam.

From the results of Test Examples 2 and 3, it is presumed that Compositions 1 to 3 had a microemulsion formulation. A review of this result and the observation result of Test Example 1 is described with reference to FIG. 4. The phenomenon in which the low light transmission region 12 expands on the foam surface is presumed to be a state in which the micelles 33 dispersed in the composition are combined and fused to the bubble shell (FIG. 4). Here, the high light transmission region 11 is in the process of adsorption/fusion of micelles, and it is presumed that phase inversion occurred from the fact that the micelles were injected into the low light transmission region 12 which appeared to be a deep color after the adsorption. Further, from the fact that the low light transmission region 12 appeared to be very dark by an optical microscope observation, it is presumed that a structure of the bubble shell in the low light transmission region 12 is a multilayer structure, and that the outermost layer of the bubble shell is in a phase different from that of the micelle (droplet) 33. Further, it is suggested that the outermost layer and the innermost layer are in phases different from the droplet 33, that is, phases containing water, i.e., aqueous ingredient phases 31 from the fact that the same phase must exist as a layer at the air interface. Thus, it has been suggested that the bubble shell has a two-phase three-layer structure (three-layer structure of aqueous ingredient phase (31)-droplet phase (32)-aqueous ingredient phase (31)).

When combining the above results, it is confirmed that the micelles could not be confirmed in the microscope images after the preparation, (1) when the micelles were allowed to stand on a slide glass for 1 hour and observed by a microscope, formation of the micelles could be confirmed, thereby confirming that the micelle had a microemulsion formulation, (2) it was confirmed that the formed micelles had uniformity by performing a centrifugal separation operation, and (3) it was confirmed that the formed foam had the high light transmission region and the low light transmission region on the surface thereof, and when the foam was allowed to stand at 25° C., an area of the low light transmission region occupying the surface area of the bubble shell expands over time so that the entire surface of the bubble shell was occupied by the low light transmission region.

Accordingly, it can be determined that the composition is suitable as a composition for a screen foamer without requiring washing and removing operations after application.

By leaving the compositions for about 1 hour, the equilibrium of the polyhydric alcohol is changed due to transpiration of water, and thus the micelles are enlarged. This formation of the micelle becomes the basis of the formation of the bubble shell, and thus it is presumed that it is important that the micelles can be observed at this point. Further, the shape maintenance to some extent and suppression of enlargement achieved by adding stress such as centrifugation of 15000 g or the like, is a factor that affects strength of the bubble shell in the two-phase three-layer structure, i.e., a structure in which the droplet phases are sandwiched between upper and lower portions in a continuous phase. As the strength of the bubble shell increases, the foam is resilient, and has strong elasticity and a long lasting time. It is considered to be resulted from the large osmotic pressure that is antagonized by the surface tension.

Example 2

Compositions 4 and 5 having the same formulation as Composition 1 but different in preparation method were prepared.

Specifically, among the prescription ingredients, from the heparin-like substance, which is a prescription ingredient, to POE-hydrogenated castor oil 60 were weighed, dissolved by heating at 65° C., stirred and cooled to room temperature, and remaining ingredients were added thereto, followed by stirring to obtain Composition 4.

Further, Composition 5 was prepared by preliminarily mixing and solubilizing ingredients other than the non-ionic surfactant, sequentially adding a non-ionic surfactant dissolved at 65° C. thereto, and cooling with stirring.

Composition 1, Composition 4, and Composition 5 were compared and observed in the same manner as in Test Example 1 in view of the forms of the foam. Results thereof are shown in FIG. 8.

In addition, Composition 1, Composition 4, and Composition 5 were observed in the same manner as in Test Example 2 in view of the composition state.

All of Composition 1, Composition 4 and Composition 5 did not show formation of micelles immediately after preparation. Meanwhile, the formation of micelles was confirmed after allowing the compositions to stand on the slide glass for 1 hour.

Figure 8:
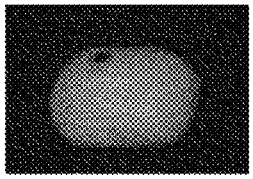
FIG. 8 shows results of comparative observation of foam morphology of Composition 1, Composition 4, and Composition 5 by the method of Test Example 1.

As shown in the upper part of FIG. 8, in Compositions 4 and 5, the discharged bubbles were rough and the maintenance rate was also low. Further, as to the surfaces of the foams formed from Compositions 4 and 5, after allowing the foams to stand, the highlight transmission region was rather observed, and the entire surface of the foam was not occupied by the low light transmission region, and the image was wholly whitish. In addition, the structure of the foam in the low light transmission region, i.e., the three-layer structure of the foam, was incomplete. Further, the bubble shell was thin.

It may be appreciated from this result that whether or not the entire foam becomes occupied by the low light transmission region, i.e., whether or not the structure of the bubble shell forms a robust two-phase three-layer structure after allowing the foam to stand is associated with whether or not a foam having good usability is formed.

These results also show that even if a composition is the same as that of the composition of the present invention capable of forming the foam of the present invention, there is a difference in a state and a structure of the foam due to the difference in the preparation method. In other words, it is possible to determine whether or not the composition becomes an excellent external preparation by precisely evaluating the structure of the foam, rather than the formulation of the composition.

These results also show that it is preferable to include a step of solubilizing the ingredients of the composition at or above the cloud point of the non-ionic surfactant as the preparation method for the composition.

INDUSTRIAL APPLICABILITY

The present invention can be applied to a product for screen foamer.

REFERENCE SIGNS LIST

10 foam
11 high light transmission region
12 low light transmission region
21 outer gas phase
22 inner gas phase
3 liquid phase
31 aqueous ingredient phase
32 droplet phase
33 droplet (micelle)

The invention claimed is:

1. A foam comprising a non-ionic surfactant, 1,3-butylene glycol, and glycerin,
    wherein the foam further comprises an air layer and a bubble shell encapsulating the air layer, wherein the bubble shell comprises a high light transmission region that is optically transparent and a low light transmission region that is less optically transparent than the high light transmission region, both regions being disposed so as to spread across a surface of the bubble shell in such a manner so as to form an identifiable boundary therebetween, and
    wherein the foam is configured so that when the foam is allowed to stand at 25° C., an area of the low light transmission region occupying the surface area of the bubble shell expands over time, and thus the entire surface of the bubble shell becomes occupied by the low light transmission region.

2. The foam according to claim 1, wherein a structure of the bubble shell in the low light transmission region is a multilayer structure composed of two or more layers.

3. The foam according to claim 2, wherein the multilayer structure is a two-phase three-layer structure including:
    an aqueous ingredient phase that is in contact with an outer gas phase of the foam;
    an aqueous ingredient phase that is in contact with an inner gas phase of the foam; and
    a droplet phase that is interposed between the two aqueous ingredient phases and contains the non-ionic surfactant and the 1,3-butylene glycol.

4. A screen foamer composition in a solulized state that forms a foam comprising a non-ionic surfactant, 1,3-butylene glycol, and glycerin,
    wherein the foam further comprises an air layer and a bubble shell encapsulating the air layer,
    wherein the bubble shell comprises a high light transmission region that is optically transparent and a low light transmission region that is less optically transparent than the high light transmission region, both regions being disposed so as to spread across a surface of the bubble shell in such a manner so as to form an identifiable boundary therebetween, and
    wherein the foam is configured so that when the foam is allowed to stand at 25° C., an area of the low light transmission region occupying the surface area of the bubble shell expands over time, and thus the entire surface of the bubble shell becomes occupied by the low light transmission region.

5. The screen foamer composition according to claim 4, wherein the composition contains a polysaccharide that is sulfated at an amount of 0.001 to 5% by mass.

6. The screen foamer composition according to claim 5, wherein the polysaccharide that is sulfated is a heparin-like substance and/or hyaluronic acid.

7. The screen foamer composition according to claim 4, wherein the composition contains the non-ionic surfactant in an amount of 1 to 15% by mass.

8. The screen foamer composition according to claim 4, wherein the composition contains a polyhydric alcohol having a hydrophobic end and/or a polyhydric alcohol polymer in an amount of 10% by mass or more.

9. The screen foamer composition according to claim 4, wherein the composition contains 0.001 to 30% by mass of the polyhydric alcohol having 2 to 6 carbon atoms in which hydroxyl groups are bonded to all the carbon atoms.

10. The screen foamer composition according to claim 4, wherein the composition contains an organic salt and/or an inorganic salt.

11. The screen foamer composition according to claim 4, wherein the composition is prepared by solubilizing ingredients of the composition at or above a cloud point of the non-ionic surfactant.

12. The screen foamer composition according to claim 4, wherein the composition satisfies the following conditions (A) and (B) when observed by an optical microscope:
(A) before the treatment of (I) or (II) below, no micelle image is observed or a micelle image is hardly observed, and
(B) after the treatment of (I) below, the micelle image is observed:
(I) the composition is allowed to stand in an open system, and
(II) stress is applied to the composition.

13. The screen foamer composition according to claim 12, wherein the composition further satisfies following condition (C):

(C) after the treatment of (II) above, the micelle image is more observed than before the treatment.

14. The screen foamer composition according to claim 13, wherein the treatment (II) is a treatment for applying stress to the composition by centrifugation.

15. A method comprising:
solubilizing ingredients of the screen foamer composition of claim 4 at or above a cloud point of the non-ionic surfactant.

16. The foam according to claim 1, wherein the non-ionic surfactant is at least one selected from the group consisting of polyoxyethylene alkyl ether, polyoxyethylene alkenyl ether, polyoxyethylene hydrogenated castor oil, polyoxyethylene fatty acid ester, polyoxyethylene sorbitan fatty acid ester, polyoxyethylene fatty acid glyceryl, polyoxypropylene polyoxyethylene alkyl ether, and polyoxypropylene polyoxyethylene alkenyl ether.

* * * * *